(12) United States Patent
Hannemann et al.

(10) Patent No.: US 11,961,382 B2
(45) Date of Patent: Apr. 16, 2024

(54) METHOD FOR OPERATING A HEARING SYSTEM

(71) Applicant: Sivantos Pte. Ltd., Singapore (SG)

(72) Inventors: Ronny Hannemann, Buckenhof (DE); Tobias Wurzbacher, Fuerth (DE)

(73) Assignee: Sivantos Pte. Ltd., Singapore (SG)

( * ) Notice: Subject to any disclaimer, the term of this patent is extended or adjusted under 35 U.S.C. 154(b) by 235 days.

(21) Appl. No.: 17/520,900

(22) Filed: Nov. 8, 2021

(65) Prior Publication Data

US 2022/0189278 A1  Jun. 16, 2022

Related U.S. Application Data

(63) Continuation of application No. PCT/EP2020/086518, filed on Dec. 16, 2020.

(51) Int. Cl.
*A61B 5/00* (2006.01)
*A61B 5/11* (2006.01)
*G08B 21/04* (2006.01)
*G08B 31/00* (2006.01)
*H04R 25/00* (2006.01)

(52) U.S. Cl.
CPC ........ *G08B 21/0446* (2013.01); *A61B 5/1126* (2013.01); *A61B 5/6815* (2013.01); *A61B 5/7275* (2013.01); *G08B 31/00* (2013.01); *H04R 25/554* (2013.01)

(58) Field of Classification Search
CPC ............... A61B 5/1117; H04R 25/552; H04R 2225/39; H04R 2225/55; H04R 25/505; G08B 21/0446; G08B 31/00; G08B 21/043
See application file for complete search history.

(56) References Cited

U.S. PATENT DOCUMENTS 10,624,559 B2 *   4/2020  Bhunia ................ A61B 5/7275
2018/0228404 A1   8/2018  Bhunia et al.
2020/0205746 A1   7/2020  Burwinkel et al.

FOREIGN PATENT DOCUMENTS

WO    2020124022 A2   6/2020
WO    2020206155 A1   10/2020

* cited by examiner

*Primary Examiner* — Brian Ensey
(74) *Attorney, Agent, or Firm* — Laurence A. Greenberg; Werner H. Stemer; Ralph E. Locher

(57) ABSTRACT

A method for operating a hearing aid system. The hearing aid system includes a hearing aid with at least one input transducer, an output transducer, and a motion sensor. The movement of a hearing aid system user is captured as movement data of the motion sensor. A probability for a future fall or trip event on the part of the hearing aid system user is determined on the basis of the captured movement data. A perceptible warning signal is generated when the probability reaches or exceeds a stored threshold value.

13 Claims, 6 Drawing Sheets

METHOD FOR OPERATING A HEARING SYSTEM

Figure 1:
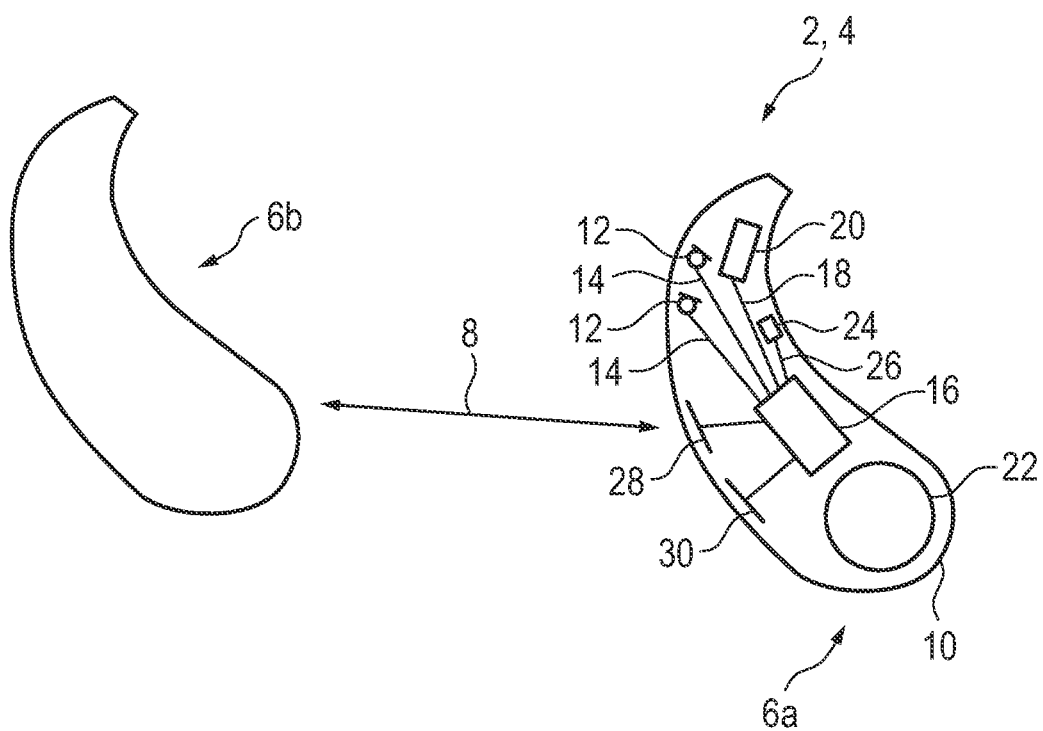

The invention relates to a method for operating a hearing aid system, which comprises a hearing aid with at least one microphone and one receiver, as well as a motion sensor. The invention also relates to a hearing aid system, in particular a hearing aid device, for carrying out the method.

Hearing aid devices are portable hearing devices that are used to provide care for deaf or hearing-impaired people. In order to meet the numerous individual needs, different types of hearing aids are available, such as behind-the-ear hearing aids (BTE) and hearing aids with an external receiver (RIC: receiver in the canal) as well as in-the-ear hearing aids (ITE), including for example conchal hearing aids or channel hearing aids (CIC: Completely-in-Channel, IIC: Invisible-in-the-Channel). The hearing aids listed as examples are worn on the outer ear or in the auditory canal of a hearing aid user. In addition, bone conduction hearing aids, implantable hearing aids, or vibrotactile hearing aids are also available on the market. In these the stimulation of the damaged hearing takes place either mechanically or electrically.

Such hearing aids generally have an input transducer, an amplifier, and an output transducer as essential components. The input transducer is usually an acoustoelectric transducer, such as a microphone, and/or an electromagnetic receiver, such as an induction coil or a (radio frequency, RF) antenna. The output transducer is usually implemented as an electro-acoustic transducer, for example as a miniature speaker (receiver), or as an electromechanical transducer, such as a bone conduction receiver. The amplifier is usually integrated into a signal processing device. The power supply is usually provided by a battery or a rechargeable battery.

In the case of a so-called binaural hearing aid device, two such hearing aids are worn by a user, with a communication link existing between the hearing aids. During operation, data, possibly even large amounts of data, are exchanged, for example wirelessly, between the hearing aids on the right and left ears. The data and information exchanged enable the hearing aids to be adapted particularly effectively to a particular acoustic environmental situation. In particular, this enables a particularly authentic spatial acoustics for the user and improves the intelligibility of speech, even in noisy environments.

As people age, there is an increasing risk of disease or comorbidities, in particular of the autonomic nervous system (ANS), such as hearing loss, dementia, or Parkinson's disease. In particular, more than one of these conditions often occur, so that people with dementia or Parkinson's typically also have a hearing impairment or hearing loss.

Many of these diseases and disorders also lead to a higher fall risk and eventually to fall events on the part of the affected person, which can lead to serious injuries. Psychological consequences or effects of fall events, such as episodes of anxiety after a fall, must also be taken into account. A fall can thus lead to a reduced quality of life and increased costs in the healthcare system. Most falls could be prevented if the risk of falls were detected early, which could maintain a high quality of life and reduce the costs to healthcare systems.

For monitoring various types of ANS disorders and for assessing the associated fall risk, it is conceivable, for example, to use motion sensors or motion detection devices (motion capture), which record and evaluate the movements or a mobility impairment of the affected person. However, additional hardware is usually required and/or an expert who will ensure reliable placement of the sensors.

However, such clinical assessments or in-patient motion capture systems have a number of disadvantages in the clinical context.

For example, the methods of fall risk assessment (FRA) commonly used in the clinical context have poor to moderate diagnostic accuracy or fall prediction in healthy, high-functioning older adults, and are dependent on the expertise of the observer.

Furthermore, due to the observer effect in controlled gait and equilibrium tests in the laboratory, monitored FRA measurements do not reflect the naturalistic and multitasking-capable behavior of the person.

A (visual) 3-dimensional motion capturing and instrumented walkways are resource-intensive and tied to specialized clinics/locations and only allow snapshots to be taken during prescribed functional tasks.

The use of environmental sensors, in particular cameras, for monitoring and recording personal movements is also conceivable. However, such environmental sensors have limitations due to visual occlusions and the tracking of the same person in rooms containing multiple people with similar physical characteristics.

There is no easy-to-use, objective and reliable diagnosis/monitoring system that can be easily managed by the user for the diagnosis and monitoring of ANS diseases. Even if a highly trained/experienced medical expert could assess the condition and progression of ANS diseases in a laboratory, there is a lack of solutions that can be applied in a patient's daily living situation. To date, older people who suffer from hearing loss and other ANS disorders need many independent solutions for each disorder separately.

The object of the invention is to specify a particularly suitable method for operating a hearing aid system. In particular, an early detection of a fall risk for the hearing aid system user is to be implemented. Preferably, the treatment of hearing disorders should be linked to the monitoring of other ANS diseases. An additional object of the invention is to specify a hearing aid system that is particularly suitable for carrying out the method.

With regard to the method, this object is achieved according to the invention by the features of claim 1 and with regard to the hearing aid system, by the features of claim 10. Advantageous embodiments and extensions form the subject matter of the dependent claims.

The advantages and embodiments mentioned in relation to the method are also applicable mutatis mutandis to the hearing aid system and vice versa. Where method steps are described in the following, advantageous configurations for the hearing aid system are obtained in particular by the fact that the latter is designed to execute one or more of these method steps.

The method according to the invention is intended for operating a hearing aid system, in particular a hearing aid device, and is also suitable and designed for this purpose. The hearing aid system has a hearing aid.

The hearing aid is used, in particular, for treating a hearing-impaired user (hearing aid system user). The hearing aid is designed to record sound signals from the environment and to output them to a user of the hearing aid. For this purpose, the hearing aid has at least one acoustic-electric input transducer, in particular a microphone, as well as at least one electro-acoustic output transducer, for example a receiver. The input transducer captures sound signals (noises, tones, speech, etc.) from the environment during operation of the hearing aid and converts them into an electrical input signal (acoustic data). An electrical output signal is generated from the electrical input signal by modifying the input signal in a signal processor. The signal processor is part of the hearing aid, for example. The input transducer and the output transducer, as well as the signal processor if present, are housed in particular in a housing of the hearing aid. The housing is designed in such a way that it can be worn by the user on the head and near the ear, e.g. in the ear, on the ear or behind the ear. The hearing aid is preferably designed as a BTE hearing aid, ITO hearing aid or RIC hearing aid.

The hearing aid also has a motion sensor to capture movements of the hearing aid system user. The motion sensor is designed and configured to detect three-dimensional (body) movements or motion events, in particular translational and/or rotational movements. The motion sensor is formed, for example, as an accelerometer and/or a gyroscope, i.e. as a gyroscopic (position) sensor. Alternatively, the motion sensor can also be a pulse, blood pressure, or light sensor. A combination of accelerometer and/or gyroscope and/or pulse sensor and/or blood pressure sensor and/or light sensor is also possible. The motion sensor is preferably integrated in the hearing aid, in particular in its housing.

The conjunction "and/or" here and in the following is to be understood to mean that features linked by means of this conjunction can be implemented both jointly and as alternatives to each other.

In the application case, the hearing aid is worn on the head and near the ear of the hearing aid system user, so that the movement sensor can be used to detect, in particular, head movements of the hearing aid user. In particular, walking movements, i.e. body movements due to walking or running, can be detected at least indirectly via the motion sensor of the hearing aid.

According to the method, during the operation of the hearing aid system, a movement of the hearing aid system user is recorded as movement data of the motion sensor. In this case, movement data is to be understood in particular as direction-dependent accelerations or rotations, in particular a movement pattern derived from them. The movement data is therefore a measure of the body movements performed by the hearing aid system user, in particular for walking movements.

According to the invention, a probability of a future fall or trip event affecting the hearing aid system user is determined on the basis of the movement data collected. In other words, the movement data is evaluated with regard to a fall risk, in particular the fall risk is predicted or estimated based on the movement data as a probability of falling or tripping, or a measure of this. A fall or trip event of the hearing aid system user is understood to mean a fall or trip, i.e. falling down or falling over or tripping, by the person wearing the hearing aid.

The terms "forecast" or "forecasting" here and in the following mean, in particular, a predictive estimate, i.e. a prediction, in which a future or expected fall risk that occurs with a sufficient probability is calculated or predicted based on current and/or past movement data—possibly with the application of mathematical or physical models. The level of probability which is considered sufficient and the specific size of the probability is initially irrelevant. This can be determined, for example, from past movement data or from appropriate tests or experiments. Different people may have different predicted fall risks due to differences in age, state of health, or body dimensions.

"Estimation" or "estimating" here and in the following refer to an approximate determination of the fall probability by evaluation of the movement data, for example using pattern recognition, pre-characterized measurements, stored tables or characteristic curves, or using statistical-mathematical methods.

According to the invention, a perceptible signal is generated as a fall or trip warning (warning signal) when the probability or the fall risk reaches or exceeds a stored threshold value. In other words, a warning is generated for the hearing aid system user if a sufficiently high fall risk is present. The level of probability or fall risk which is considered sufficient and the specific size of the probability is initially irrelevant. This can be determined, for example, from past movement data or from appropriate tests or experiments. Different threshold values may be found for different people due to differences in age, state of health, or body dimensions.

The warning signal is, for example, an optical and/or acoustic signal, such as an illuminated or flashing LED or a warning tone or warning sound, generated by the hearing aid or the output transducer. A haptic vibration signal, for example, is also conceivable, which is generated, for example, by an auxiliary device connected to the hearing aid for signal transmission, in particular a smartphone. In addition or alternatively, the warning signal could also be sent to a doctor or carer via an application linked to the hearing aid, such as a smartphone app. The warning signal can also be a combination of acoustic, optical and haptic signals.

The warning signal informs the user of the hearing aid system about the danger or risk of a fall while wearing it. The hearing aid system user thus receives a signal that there is an impending danger of a fall event. Thus, the risk of a fall or fall event is advantageously reduced. As a result, a particularly suitable method for operating a hearing aid system is implemented. The method according to the invention thus provides a particularly advantageous fall or trip protection.

The motion sensor in the hearing aid, which is worn to compensate for hearing loss, is thus used according to the invention to monitor the movement patterns of the hearing aid wearer, and a fall risk is determined from this. A key idea of the invention is thus, in particular, to capture the movements of the hearing system user (e.g. gait, rotation, etc.) using the hearing aid, as well as to analyze the captured movements and evaluate them with regard to a fall risk.

The analyzed or evaluated movement data allow, for example, a characterization of a progressive ANS disorder. In principle, early detection or diagnosis of ANS disorders is also possible by the determination of a fall risk according to the invention. This means that the method can be used as part of the diagnosis or treatment of ANS disorders. However, the diagnosis or treatment of ANS disorders is not part of the claimed invention.

The hearing aid has a memory, for example, and is designed to store the movement data captured by the motion sensor within a time window in the memory and to evaluate it with regard to the fall risk (monitoring) at a later time. The hearing aid is thus designed, for example, to store temporally bounded extracts of the motion sensor signal in the memory and to output them in particular for determining the probability of a fall. The hearing aid therefore has a recording function for the movement data. It is convenient for the recorded movement data to be transferable from the memory to an external data source via an interface. The time window has a length of at least 1 min (minute) to 1 d (day), for example, particularly preferably a length in the range of 1 h (hour) to 12 h. Other lengths are also suitable, however. In particular, a time window is used that corresponds to the period for which the hearing aid is worn. This means that recording starts when the hearing aid is put on and ends when the hearing aid is removed.

An event-based recording and evaluation is also conceivable, in which an (operating) algorithm detects, for example, whether and when the hearing aid system user is walking. If no walking is detected, a simple and energy-saving mode is preferably applied, wherein during walking the sampling rate is increased and further calculations, analysis and storage operations are carried out based on the raw sensor data. This means that the time window can be adjusted/triggered dynamically based on detected body movements. This enables a longer observation/evaluation window, for example, over more than one day.

Furthermore, it is possible, for example, to provide a periodic or regular time window for monitoring and evaluation, for example, only a maximum of one period per day or week is recorded, wherein an algorithm captures, for example, a time window of 10 minutes only once per week.

For example, the motion analysis and risk prediction uses macro- and microevents, which characterize the gait of the hearing aid system user and are additionally categorized into rotations and transitions between the movements.

A "microevent" here and in the following is to be understood in particular to mean a characterization of (motion) features of a movement, i.e. a movement sequence or a movement pattern. A "macroevent" here and in the following is to be understood to mean in particular a plurality of movements or groups of movements within a time interval, for example on one day, i.e. a movement sequence or series of movements.

For example, a macroevent is the number of steps per time interval, i.e. the number of steps per day or the number per action in the case of a predefined test for characterizing the intensity (cadence, step frequency).

A macroevent is also an absolute and relative time expenditure per classified activity, i.e., for example, walking time spent per day, a percentage of walking and non-walking, an absolute duration of the longest walk taken, or the like. This is based on the recognition that a total walking time for potential individuals at risk of falling is often reduced compared to individuals who are not at risk. Furthermore, the total time spent on so-called sedentary behaviors is usually longer for people at risk of falling.

Macroevents are also low-motion behaviors, such as standing, sitting, or lying. For example, these can be expressed in terms of a total time spent on each of these behaviors per day, for example. Likewise, a duration for the adoption of these behaviors, i.e. a duration for sitting-down or standing-up movements, can be used to characterize these behaviors. Here, for example, an average value or maximum value or percentile, in particular a 90% percentile, can be determined from multiple standing-up or sitting-down movements for qualification. Furthermore, variability of the time per day and duration of the sedentary behavior can be taken into account.

Macroevents are also understood to mean, for example, a variance of the movements from day/action to day/action over a period of time in order to characterize the quality of the movements. For example, the progression of dementia is characterized by an increase in day-to-day variability of gait patterns, from which a fall risk can be derived.

A microevent as used here is, for example, the tempo of a movement, for example a step speed or "walking speed", or a stride length variability. Those at risk of falls walk more slowly, wherein changes in walking speed, as explained above, can be characteristic of progression in dementia. The walking speed can be analyzed in predefined (time) intervals, for example, less than 10 s (seconds), 10 s to 60 s, 60 s to 120 s, longer than 120 s. A rough estimate of the speed is sufficient, it is not necessary to measure or determine the speed accurately in meters per second (m/s). To determine the tempo or the velocity, the movement data can be analyzed as raw values or in the form of RMS values.

A step movement (pace), for example, i.e. the step length, can also be understood as a microevent. The step length can decrease as dementia progresses, so that a fall risk can be predicted from a determination or estimate of the step length. For example, a step length estimate for hip or chest-worn motion sensors is described in the publication Analogue Devices Application Note, AN-602, entitled "Using the ADXL202 in Pedometer and Personal Navigation applications" by H. Weinberg.

For example, a rhythm of the movement, such as pace, stride and standing time, or an asymmetry of the movement, i.e. a variability of pace, stride and standing time, is also understood as a microevent. In the case of an asymmetry, for example, the step, stride and standing time variability can characterize parameters of a movement feature known as "gait smoothness" (i.e. a "step-to-step" symmetry, a gait stability, or a harmonic ratio, HR).

If the method is used, for example, in the context of a diagnosis or treatment of ANS disorders, a heart rate of the hearing aid system user can be analyzed separately in parallel with the method, for example in the antero-posterior (AP), medio-lateral (ML) and superior-inferior (V) directions, according to the direction of travel. For example, the heart rate is reduced in early stages of dementia, with changes in Parkinson's disease being significantly correlated with a patient's cognitive status, in particular the heart rate in the AP direction.

A postural monitoring for monitoring the posture of the hearing aid system user can also serve as a microevent. For example, a step or step-length asymmetry is used to check posture characteristics and/or (posture/movement) stability of the hearing aid system user.

Another microevent, for example, is a variability of the step length and/or step speed within and between different movement patterns, for example during a walk.

Furthermore, a variability of a standing and/or step time is to be treated as a microevent, which can also occur between and within comparable actions or movements.

A microevent can also be a different type of variability of the gait pattern, characterized by spectral-temporal (power) distribution patterns in different frequency bands for each direction (in other words, antero-posterior (AP) according to the direction of travel, medio-lateral (ML) and superior-inferior (V)) or by autocorrelations in dominant dimensions.

The temporary changes in user-typical variations of the above-mentioned "features" or movements (variability of step length and/or step speed, variability of a standing and/or step time, variability of the gait pattern) can characterize compensatory equilibrium reactions of the hearing aid system user, which are necessary to avoid falls. Such compensatory equilibrium reactions can be characterized, for example, as "mis-step" stumbles, slips or trips, wherein, for example, an increase in the frequency of such compensatory equilibrium reactions results in a higher fall risk.

The movement analysis also includes evaluation of turning or rotation behaviors of the hearing aid system user. People with an increased fall risk usually exhibit a longer turning time during turning movements, and they also perform turning movements less frequently and show inconsistent turning angles with large variance for the same movements. An increased fall risk can also be manifested in a reduced consistency, both in the angular size of the turn/turning movement and in the time of a large turn, over a period of days.

To analyze or evaluate the turning behavior, for example, the following features are extracted and/or analyzed from the movement data: the rotation duration, the rotation velocity peak, a number of steps during the rotation, a rotation angle in categories (quarter, half, full turn; or similar categories of rotation angles), a number of rotations per above category per day, a variance of the number, angle and/or speed of the rotations over consecutive days. In binaural hearing aids, the features of the individual devices extracted from the movement data can be combined to better characterize the rotation.

For example, the movement data can be captured and evaluated in discrete time intervals. Preferably, however, during the operation of the hearing aid system, in particular while the hearing aid is being worn or during the time window, an essentially continuous or uninterrupted acquisition and analysis of the movement data takes place. In this context, essentially continuous or uninterrupted means in particular quasi-continuous, i.e., that in the case of a digital acquisition and evaluation, for example, the measuring frequency/speed of the motion sensor is higher, in particular at least twice as high, as the frequency or speed of a bodily movement to be captured.

A (quasi-)continuous movement monitoring/analysis and the determination of the fall risk enable an analysis or diagnosis of ANS disorders, which can be carried out even by a non-specialized person (e.g. nurse, physiotherapist, doctor; not just by medical experts) in a clinical/outpatient setting and under very ecological conditions in a relatively short time. It enables the healthcare professional to develop individual approaches to rehabilitation strategies that ensure safer navigation and a reduction in falls and the associated costs.

Continuous acquisition and evaluation of the movement data also enable reliable monitoring if the movement patterns change over time (improve/worsen). This makes it possible to give the hearing aid system user direct and appropriate feedback so that they can react in good time. Thus, it is not necessary to have a doctor's appointment to monitor or review changes in the movement patterns, which results in lower costs in the healthcare system.

A (continuous) assessment using motion sensor information in hearing aids shows improved diagnostic accuracy of the natural or disordered behavior compared to other methods for assessing gait/turning patterns.

In addition, the method according to the invention is comparatively economical, since only wearable sensors are used in a device which is worn anyway to compensate for hearing loss. The method according to the invention thus provides an advantageous extension of the function of the hearing aid in addition to treating a hearing-impaired user.

Compared to environment sensors such as cameras installed in buildings, information or movement data from wearable hearing aid sensors has a greater benefit beyond the living space; in particular, it is not necessary for the user to be in a monitored environment, since they carry the sensor system around with them.

Due to the method according to the invention, it is also not necessary for the hearing aid system user with an ANS disorder to carry an additional device. In other words, there is no additional burden of using another device in addition to the hearing aid. This can thus also contribute to persuading only slightly hearing-impaired persons to use a hearing aid to improve their quality of life and to prevent injuries and/or to monitor fall risks.

Hearing aid-based diagnostics using the method according to the invention could also be of benefit for evaluating disorders according to clinical protocols in which time and patterns for dedicated actions are analyzed (for diagnostic purposes). Such protocols include, for example, sitting down, standing up (sit-to-stand test), staying in a standing position with open and closed eyes, or structured test procedures such as the so-called Tinetti test (see, for example, Tinetti M. E., Performance-oriented assessment of mobility problems in elderly patients, J Am. Geriatr. Soc. 1986; 34:119-126).

In an advantageous embodiment of the method, personal health data of the hearing aid system user is stored in a memory of the hearing aid system user, wherein the probability of falling is determined on the basis of the stored health data. This means that the stored health data is also taken into account in the evaluation or analysis of the movement data for determining the fall risk. In addition or alternatively, it is also conceivable, for example, that the threshold value is varied on the basis of the health data.

This embodiment of the method is based on the recognition that age-related disorders or ANS disorders alter several major features of the gait pattern. This enables a particularly reliable and safe estimation or determination of the fall risk, so that an early and timely warning for the hearing aid system user is guaranteed.

In other words, the recorded movement data is analyzed together with other (available) information about the user (i.e. cognition, hearing, environment, cardiovascular status) to enable a user-specific characterization. This characterization is used to predict changes in the fall risk associated with certain disorders, but also to monitor the progression of these disorders.

Health data here is understood to mean personal information about the individual hearing aid system user, in particular physiological and medical/health data of the hearing aid system user, such as age, height, leg/step length, weight, cardiovascular status, cognitive status, hearing ability, activity of the patient's own voice, tinnitus. This enables a reliable determination of the micro- and macroevents in the course of the movement analysis of the movement data.

Preferably, the health data also includes information about any health-related mobility impairment of the hearing aid system user. A "health-related mobility impairment" in this case means in particular a medical incapacity, a health-related handicap, or a health condition of the hearing aid system user, which temporarily impairs or restricts his/her movements and thus (intermittently) causes an increased fall risk. Such an incapacity can be, for example, an injury that requires the use of a walking support or walking aid. In particular, this is understood to mean an incapacity in the form of a cognitive disorder, in particular a disorder of the autonomic nervous system (ANS), such as hearing loss, dementia, epilepsy or Parkinson's disease.

The stored health data makes it possible, for example, to carry out the movement pattern analysis with regard to dementia or vertigo, and thus to enable a more precise determination of the fall risk. In particular, it is thus possible to output the warning signal to the hearing aid system user as feedback in a timely manner.

The stored health data provides a more comprehensive picture of the hearing aid system user for the movement analysis and risk determination, since not all information about an ANS disorder is to be found in its specific gait pattern. Furthermore, it is possible that a hearing aid system user may suffer from more than one disorder. In order to find optimal solutions and to avoid false attributions, it is necessary to consider as much available information as possible, even beyond gait patterns and their changes, in determining the risk. Furthermore, the stability and reliability of the predictions are increased and misclassifications in case of noisy data are avoided.

If available, data from other sensors connected to the hearing system for signal transmission, such as photoplethysmography (PPG), electroencephalography (EEG), or electromyography (EMG), can also be taken into account, which provide information about cardiovascular status (i.e. frequency, heart rate variability) or stress measurements, for example.

According to the invention, a hearing aid parameter and/or a hearing aid performance of the hearing aid is/are adjusted depending on the determined probability. This means that the hearing aid settings related to signal processing and output of an ambient signal are varied as the fall risk changes. In particular, the settings are adjusted or changed in such a way that the fall risk is minimized as far as possible. This ensures a particularly safe and effective fall protection.

Additionally or alternatively, a hearing aid parameter and/or a hearing aid power of the hearing aid is adjusted depending on the stored health data. In a suitable extended embodiment, for example, the "classification" for the automatic hearing aid program is adapted according to the user profile (health data), resulting in a matched and suitable hearing aid output.

For example, people with mild cognitive impairments or dementia also suffer from poor concentration, i.e. a difficulty in maintaining focus or a slight propensity to distraction. If the gait analysis performed by the hearing aid shows a progression of the mild cognitive impairment or dementia based on an increased fall risk, the hearing aid performance can therefore be adjusted for better orientation in complex acoustic environments.

For example, a beamformer or beamforming pattern of the hearing aid is adjusted. "Beamforming" means, in particular, a directional characteristic of the hearing aid, i.e. that a directional hearing is implemented so that sound sources from a certain direction are amplified relative to other directions. For this purpose, a beamformer is used which combines the input signals of a plurality of different input transducers (microphones) in particular of the same individual hearing aid (individual device) in a suitable way to form an output signal.

To compensate for concentration weaknesses or distractibility, it is possible, for example, to adjust the compression for the posterior hemisphere in the signal processing by lowering the first knee point and to increase the compression ratio. The compression system for the anterior hemisphere can remain unchanged. In addition, the noise reduction can be parameterized for a stronger effect. This exemplary adjustment of the hearing aid settings/parameters allows for easier focusing and fewer distractions due to acoustic input from the posterior direction.

In the field of hearing aids, for example, compression is a means of adapting the hearing signal to the restricted hearing ability of a hearing-impaired person. The hearing ability of a hearing-impaired person has a restricted dynamic range, so that low input levels need to be highly amplified. However, for high input levels, the gain must be decreased because the amplified hearing signals are otherwise perceived as unpleasantly loud. The compression of the dynamic range of the audio signal counteracts this by means of an amplification with a level-dependent gain factor. In most cases, the compression characteristic, represented by the characteristic curve which specifies the ratio of input level to output level, has a linear gain of a constant factor up to a certain threshold value of the input level, while for input levels beyond the threshold value the gain is reduced depending on the level. If input level and output level are plotted against each other in decibels, this results in a compression characteristic in the form of a curve with linear sections, wherein the characteristic curve has a lower gradient above the threshold value for the input level (knee point).

For optimal treatment of hearing loss and ANS disorders, the hearing aid system parameters that influence hearing aid performance are adjusted accordingly. The analysis can also be used to control interventions which are controlled by an auxiliary device connected to the hearing aid for signal transmission, for example via a connected smartphone, in order to enable timely intervention, to facilitate the implementation of individual needs of the hearing aid system user and to counteract the progression of age-related disorders.

Preferably, the hearing aid parameters that affect hearing aid performance are adjusted on the basis of the determined fall risk. The adapted hearing aid output (output signal) could be seen as a contribution to an intervention (for example in the case of dementia or other disorders) if required. The resulting modified output signal allows, for example, a better orientation or a reduction of distractors/diversions or the like. For this purpose, multi-source compression schemes (CK, CR, gain, attack & release times, noise suppression algorithms) and monaural and/or binaural beamformer patterns are changed in the signal processing.

In a preferred embodiment of the method, an environmental situation of the hearing system user is determined on the basis of acoustic data of the input transducer (input signal). An environmental situation in this context is in particular an acoustic environmental situation or an auditory situation. The environmental situation is identified and described, for example, by means of situation detection and/or at least one level measurement and/or at least one algorithm of the hearing aid or the signal processing. For example, the environmental situation is classified according to specified criteria, and each of these classes is assigned a specific setting of the hearing aid parameters and/or hearing aid performance.

The current environmental situation is assigned to the current movement data and stored in a memory. This means that for the evaluation or risk determination on the basis of the movement data, the respective environment of the hearing aid system user can also be taken into account, thus enabling a more accurate and reliable determination of the fall risk. Preferably, the acoustic environmental situation is determined in parallel with the recording of the movement data.

In an advantageous design, to determine the probability the movement data for a particular environmental situation is compared with stored movement data and environmental situations. In other words, a comparison is made with previous analysis results and movement patterns in comparable and/or different hearing situations. This allows, for example, a fall event or near-fall event in an earlier hearing situation to be taken into account for future hearing situations, so that in such hearing situations an increased fall risk is expected.

Additionally or alternatively, for example, a comparison is possible with other similar user data which is stored anonymously in a "cloud", a remote server, or a data store.

In an advantageous design, a user profile for the hearing aid system user is created based on the stored movement data and environmental situations. In other words, the hearing aid system user is "classified" to a profile based on the stored data. This enables a daily routine detection to compare a current result with previous results, and thus to track and detect changes. The user profile enables an improved and more robust determination of the fall risk.

An additional or further aspect of the invention provides that the hearing aid is binaural and for this purpose has two individual devices, each having at least one input transducer and at least one output transducer, and thus being designed to detect sound signals from the environment and to output them to a user of the hearing aid. In addition, each of the individual devices has a motion sensor. The movement data of the individual devices are evaluated separately and then combined to determine the probability.

For example, a wireless interface is provided for data exchange between the two individual devices. For example, the wireless interface is a Bluetooth interface or a WLAN interface or a MI interface (MI-Link, MI: Magnetic Induction). For example, the Bluetooth interface is a standard or a low-energy Bluetooth interface.

As an alternative to a binaural hearing aid however, a monaural hearing aid with only one individual device is also suitable. The statements relating to a monaural hearing aid are transferable mutatis mutandis to a binaural hearing aid and vice versa.

For example, it is also conceivable that a probability is determined for the data of each of the individual devices. Preferably, however, the motion sensor information of the two individual devices is analyzed separately and then "combined", which also enables the identification or detection of complex movement patterns which are associated with progressive ANS disorders. As a result the determination of the fall risk is further improved.

In a binaural hearing aid, the two individual devices are worn by the user on different sides of the head, so that each individual device is assigned to one ear. Thus, the left and right motion sensors (3D accelerometers) are arranged at a distance from the center of the body, so that the information provided by both can be combined to characterize tangential and radial forces that indicate a rotation. This makes it possible, for example, to dispense with a position sensor or gyroscope. In addition, the two independent sensor outputs enable increased reliability of the movement data. For example, the information is only used for the risk assessment when both motion sensors indicate the same event or the same change.

In a suitable embodiment, the movement data and/or the probability are transmitted to an auxiliary device connected to the hearing aid for signal transmission. This makes it possible, for example, to display analyzed symmetries or other key metrics of the gait as well as status and changes, in an app, a website or a piece of software.

The auxiliary device is preferably a mobile operating and display device, for example a mobile phone, in particular a mobile phone with a computer function or a smartphone, or else a tablet computer. The auxiliary device is suitably equipped with a stored application software (operating software), which is used, for example, to generate the warning signal when the probability reaches or exceeds the threshold value. The application software is preferably installed or can be installed on the operating and display device as a so-called app or mobile app (mobile application, smartphone app).

This extension is based on the consideration that modern operating and display devices, such as smartphones or tablet computers in particular, are widely used in modern society and are generally available and accessible to a user at all times. In particular, the user of the hearing aid system is highly likely to have such an operating and display device in his/her household.

Today, modern smartphones are additionally equipped as standard with a plurality of different near-field and far-field communication means, which in principle makes it a simple matter to establish a communication or signal connection to the hearing aid. The application software is preferably also suitable and configured for setting operating parameters of the hearing aid, such as a sound volume. As a result, the user does not need an additional, separate operating system for monitoring and adjusting the hearing aid system, but it is possible to use his/her existing smartphone to evaluate the movement data and determine the fall risk by (subsequently) downloading and/or installing the application software. In this way, user-side costs are reduced in an advantageous way. In this case, it is possible, for example, that the health data is stored in a memory of the auxiliary device or smartphone.

The surfaces of smartphones or tablet computers, which are typically implemented as touch screens (screen, display), also allow a particularly simple and intuitive operation of the application software of the auxiliary device thereby formed. This means a smartphone or tablet computer can be particularly cost-effectively retrofitted for monitoring the fall risk.

The operating and display device comprises an internal controller, at least the core of which is formed by a microcontroller with a processor and a data store in which the functionality for carrying out the method is implemented as software in the form of the application software, so that the method or determination of the fall risk—possibly in interaction with the user—is carried out automatically when the application software is executed in the microcontroller.

The auxiliary device can be designed to transmit data to the hearing aid from a digital assistant, provided by the external data source. In particular, a digital assistant is understood to mean a voice control system that recognizes voice commands from the user and can perform and does perform various functions or actions depending on the voice command. In other words, the digital assistant is particularly designed for speech recognition, for speech analysis, for information searching or for performing simple tasks, or a combination of these. In particular, the digital assistant forms an interface between the user and another device, in particular the external data source. In particular, the digital assistant outputs data intended for the user, in particular in the form of speech. This data, i.e. an output of the digital assistant and specifically a speech output of the digital assistant, is then transmitted via the auxiliary device to the hearing aid for output to the user. In this way, feedback and information output are advantageously enabled from the digital assistant to the user. Specifically here, but also generally, the external data source is preferably the cloud.

For example, the auxiliary device can therefore be used to request user feedback based on the analysis or risk result. The user feedback could, on the one hand, refine the action performed by the hearing aid system in the event of an uncertain analysis result and/or, on the other hand, enable an algorithmic improvement of the movement analysis by recording a label for the recorded movement. In this process, the hearing aid system "learns" to recognize specific movement variations for the individual user or to improve the classification of movements for the general population based on user feedback. The feedback can be acquired by means of an app, voice commands, or other interactions with the hearing aid system.

The analysis results can also be made available to the healthcare provider and/or a medical expert to support the one-off diagnosis and continuous monitoring of age-related disorders, as well as to detect specific changes in the movement pattern at an early stage.

The analysis of the movement data can be carried out in the hearing aid and/or remotely in the auxiliary device or smartphone connected to the hearing aid. In the latter case, the raw or pre-processed movement data is preferably sent to the connected smartphone. If the analysis is performed on the smartphone, it is necessary to return the fall risk result to the hearing aid. For example, it is also possible that the threshold comparison is also performed by the auxiliary device, in which case the auxiliary device generates the warning signal and/or transmits a signal triggering the warning signal to the hearing aid.

In other words, one way of carrying out the method is for the processing and evaluation of the movement data necessary for the risk determination to be carried out in the hearing aid. Another possibility is that the hearing aid only collects the relevant movement/acoustic data, optionally stores it in a buffer, and transfers the raw data (or pre-processed data) to the (hearing-aid) external auxiliary device or smartphone of the hearing aid system for final analysis. This could take advantage of both the computing power of the smartphone and cloud services.

This results in the particular advantage that the load on the hearing aid is reduced so that the requirements for signal processing or electronics in the hearing aid are advantageously reduced. The functionality of the movement analysis, in particular the risk determination, can thus be transferred completely or partially to the auxiliary device, so that the hearing aid saves energy accordingly.

In one possible embodiment of the method, measures to reduce the fall or trip risk are indicated on the accessory device when the threshold value is reached or exceeded. In other words, the hearing aid system user will be presented with hints or suggestions on the auxiliary device that are aimed at reducing the fall risk. These measures are also referred to in particular as counselling or advice. A basic idea here is to provide the user with hints and suggestions that contribute to a further reduction of the fall risk, but which are not within the sphere of influence of the hearing aid.

For example, the movement data (including analysis) is sent to the auxiliary device or smartphone to offer treatments and tips provided by the smartphone app. Based on the gait/risk analysis, for example, the smartphone recommends actions intended to help maintain or increase physical fitness to reduce the fall risk, or to slow down cognitive decline, or to facilitate healthy aging or good quality of life, or support other interventions, such as doses of pharmaceutical products.

Furthermore, it is possible, for example, for the hearing aid system user to receive daily updates and tips on healthy aging, cooking recipes et cetera, via their smartphone app. If the output of a gait analysis performed by the hearing aid indicates a deterioration in a known disorder, a change in the movement pattern associated with increased frailty or an increase in the fall risk, the content of the tips presented by the smartphone app could be adapted to maintain or increase the current level of quality of life in order to allow autonomous living for as long as possible. For example, the smartphone app could recommend measures to help prevent further progress of the frailty (i.e. exercises, going for walks, etc.), a dietary change to avoid side effects, or to inform of the need for a doctor's visit to adjust the medication, et cetera. In this way, the hearing system could contribute to avoiding high costs in the healthcare system by pro-actively helping to keep people healthier, more mobile, and more independent.

In a possible design of the method, the movement data for determining the (fall) probability is acquired during a pre-scribed movement pattern of the hearing aid system user. In particular, a prescribed movement protocol is performed by the hearing aid system user during the acquisition. This design is particularly useful in the field of clinical, diagnostic, or therapeutic applications. In particular, it is thus possible to achieve better comparison with other patients, so that an improvement in the assessment of the fall risk is possible.

Advantageously, the movement analysis is explicitly triggered by the user, and in addition the movement analysis also takes place in particular in a controlled environment with a clear horizon of expectations about the upcoming movement. This can intensify the sampling and processing of movement patterns, wherein after the exercises a normal processing mode is thus used to reduce the power consumption. In other words, during the prescribed movement pattern, the movement data is preferably acquired with a higher resolution or higher measuring rate, so that even small deviations or disturbances are reliably detected. This improves early detection for deterioration in ANS disorders, thus enabling a particularly reliable fall protection.

For the analysis of movement patterns, for example, a number of movement categories are covered. For example, "stationary exercises", which can be performed by the patient/user either alone or under the supervision of a nurse or therapist, are ideally carried out in a daily routine. These exercises can be app-led, which means that the exercises are displayed on the auxiliary device, for example, and performed by the hearing aid system user. Possible exercises (but not a complete list) are: sit-to-stand test, vibration analysis, lifting of objects, shoelace tying, laying down/standing up, turning round.

In addition or alternatively, a permanent, continuous monitoring is performed outside the prescribed movement patterns, in which all movement patterns are continuously analyzed, evaluated and categorized. This is advantageous for creating a user profile and the overall distribution of the movement-related activities. It requires less user interaction, but is comparatively computationally intensive. Therefore, continuous monitoring for a specific time interval is also possible, which can be triggered by a key event, on a timed basis, or at user request, for example.

Preferably, environment/movement patterns are continuously analyzed for basic movements, for example, walking. When walking is detected, the next processing hierarchy is activated which analyzes the gait and its symmetry more closely. This can be carried out for a certain period of time, for example several minutes, or until the walking stops. It could be designed to perform this movement analysis for a defined or specifiable number of days.

The hearing aid system according to the invention is designed in particular as a hearing aid device and comprises a hearing aid. The hearing aid has at least one input transducer for receiving an acoustic ambient signal, and one output transducer for outputting an acoustic signal, as well as a motion sensor for capturing a bodily movement of a hearing aid system user.

The hearing aid system also has a controller, i.e. a control unit. For example, the controller is integrated into the hearing aid and is part of a signal processor, for example. In addition or alternatively, it is also conceivable that the controller is part of an auxiliary device, in particular a smartphone, connected or coupled to the hearing aid for signal transmission.

The controller in this case is generally configured—in software and/or circuit technology—for carrying out the method according to the invention described above. The controller is thus specifically configured to analyze or characterize a user movement or movement event in order to analyze in particular the progression of age-related disorders and the associated change in the fall risk.

In a preferred embodiment, the controller, at least in essence, is formed by a microcontroller with a processor and a data store, in which the functionality for carrying out the method is implemented as software in the form of operating software (firmware), so that the method—possibly in interaction with a device user—is carried out automatically when the application software is executed in the microcontroller. As an alternative within the scope of the invention, the controller can also be formed by a non-programmable electronic component, such as an application-specific integrated circuit (ASIC), in which the functionality for carrying out the method according to the invention is implemented in circuit technology.

Figure 2:
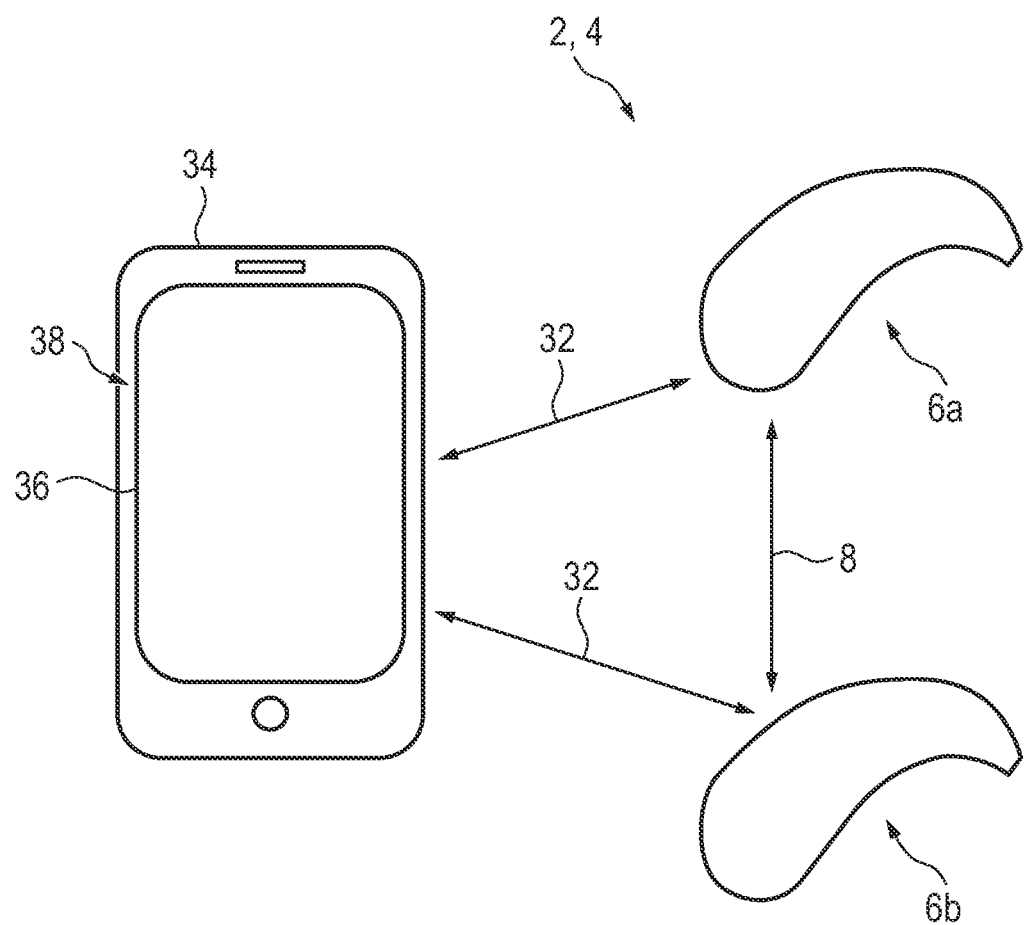
Figure 3:
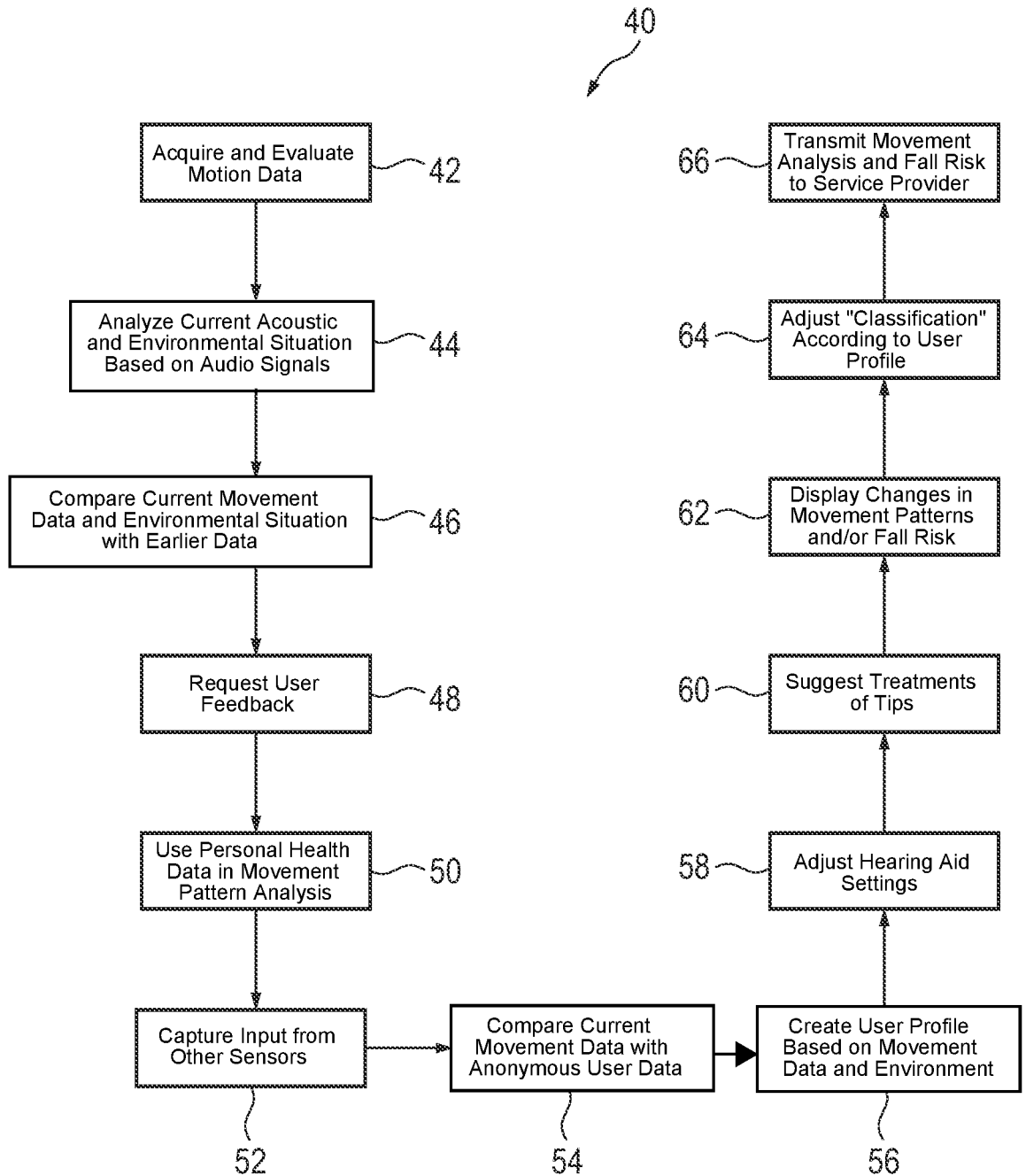
Figure 4:
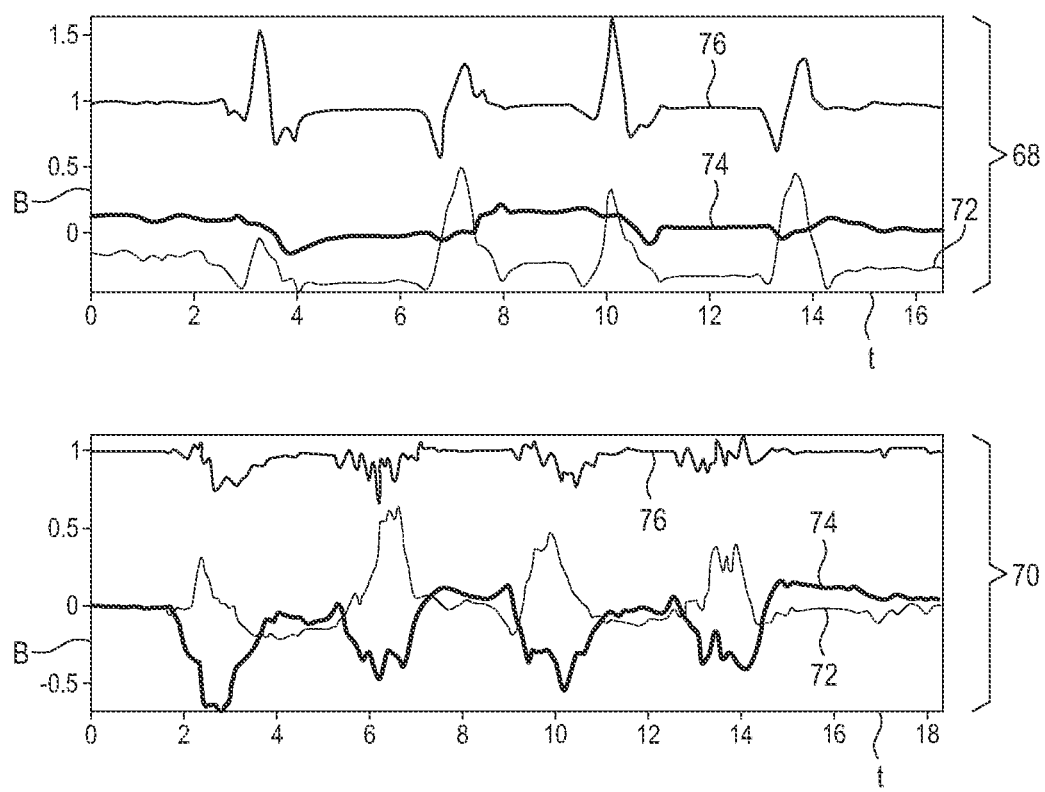
Figure 5:
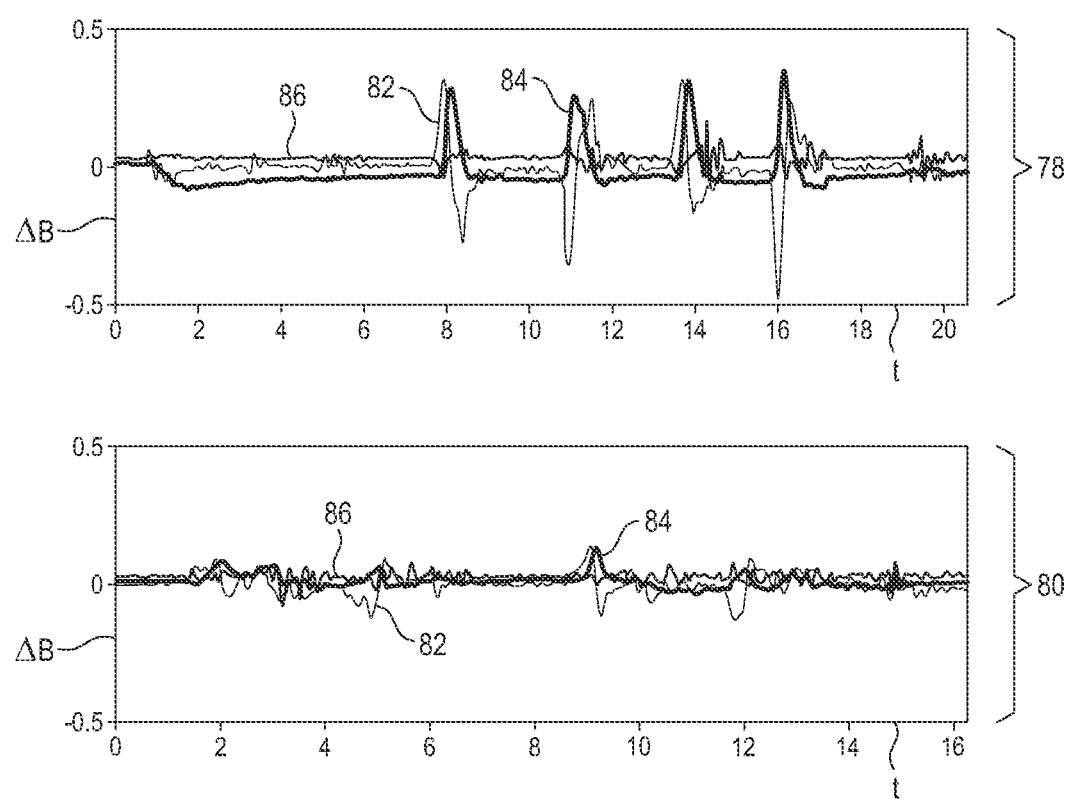
Figure 6:
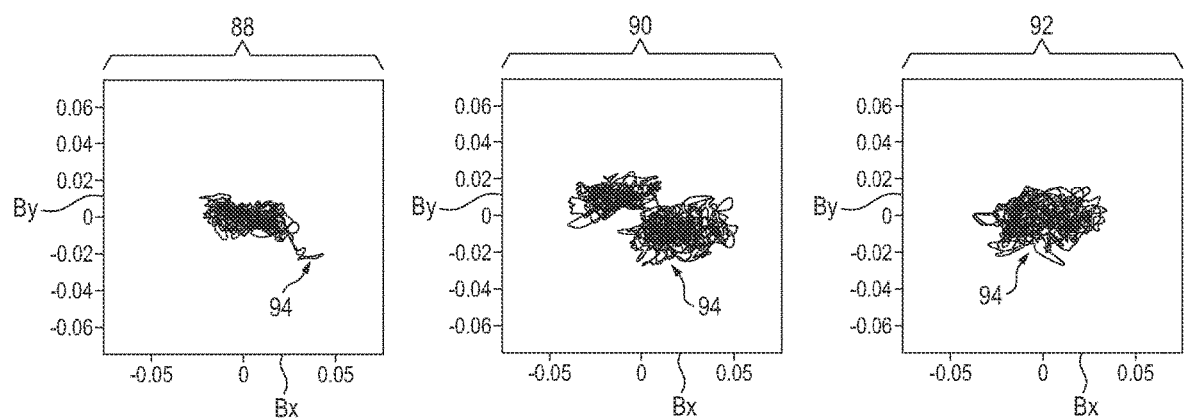

In the following, exemplary embodiments of the invention are explained in more detail based on a drawing. In the drawings, in schematic and simplified illustrations:

FIG. 1 shows a hearing aid system with a binaural hearing aid,

FIG. 2 shows the hearing aid system according to FIG. 1, in which the hearing aid is connected to a mobile auxiliary device for signal transmission, and FIG. 3 shows a flowchart of a method for operating the hearing aid system, FIG. 4 shows two time-acceleration diagrams for a sit-to-stand test, FIG. 5 shows two time-acceleration diagrams for a turn-around test, and FIG. 6 shows three acceleration-acceleration diagrams for a standstill test.

Equivalent parts and dimensions are provided with identical reference signs in all figures.

FIG. 1 shows the basic structure of a hearing aid system 2 according to the invention. In this exemplary embodiment, the hearing aid system 2 is designed as a hearing aid device with a binaural hearing aid 4 with two hearing aid devices or individual devices 6a, 6b coupled together for signal transmission. The individual devices 6a, 6b are designed, for example, as behind-the-ear hearing aids (BTE). The individual devices 6a, 6b are or can be coupled to each other for signal transmission via a wireless communication link 8.

For example, the communication link 8 is an inductive coupling between the individual devices 6a and 6b, or alternatively the communication link 8 is implemented for example as a radio link, in particular as a Bluetooth or RFID link, between the individual devices 6a and 6b.

The design of the individual devices 6a, 6b is explained below using the individual device 6a as an example. As shown schematically in FIG. 1, the individual device 6a comprises a device housing 10 in which one or more microphones, also referred to as acousto-electric input transducers 12, are installed. Via the input transducers 12, a sound or the acoustic signals in an environment of the hearing aid system 2 are detected and converted into an electrical audio signal as acoustic data 14.

The acoustic data 14 is processed by a signal processing device 16, which is also arranged in the device housing 10. Using the audio signal 14, the signal processing device 16 generates an output signal 18 which is routed to a loudspeaker or receiver 20. The receiver 20 here is designed as an electro-acoustic output transducer 20, which converts the electrical output signal 18 into an acoustic signal and outputs it. In the case of the BTE individual device 6a, the acoustic signal is transmitted to the eardrum of a hearing aid system user via a sound tube or external receiver, not shown in detail, which is connected to an earmold fitted in the ear canal. However, an electro-mechanical output transducer is also conceivable as the receiver 20, as in a bone conduction receiver, for example.

The power supply of the individual device 6a and in particular of the signal processing device 16 is provided by means of a battery 22 accommodated in the device housing 10.

The signal processing device 16 is coupled with a motion sensor 24 of the individual device 6a. The motion sensor 24 acquires acceleration and/or rotation movements of the individual device 6a during operation and sends them to the signal processing device 16 as movement data 26 during operation. For example, the motion sensor 24 is designed as a 3D acceleration sensor. In addition or alternatively, the motion sensor is designed as a position sensor, in particular as a gyroscopic sensor.

The signal processing device 16 is also connected for signal transmission to a first transceiver 28 and to a second transceiver 30 of the individual device 6a. The transceiver 28 is used to transmit and receive wireless signals via the communication link 8 and the transceiver 30 is used to transmit and receive wireless signals using a communication link 32 to a hearing-aid-external auxiliary device 34 (FIG. 2). For example, it is also conceivable that only one transceiver is provided for both communication links 8, 32.

In the exemplary embodiment of FIG. 2, the auxiliary device 34 is designed as a separate, mobile operating and display device, which is or can be coupled to hearing aid 4 for signal transmission via the communication link 32. The auxiliary device 34 shown schematically in FIG. 2 is, in particular, a smartphone. The auxiliary device 34, also referred to as hereafter as a smartphone, has a touch-sensitive display unit (display) 36, which is also referred to as hereafter as a touch screen. The smartphone 34 is conveniently introduced into the transmission range of the communication link 32. The coupling for signal transmission between the smartphone 32 and the transceivers 30 of the individual devices 6a and 6b is carried out via an appropriate integrated transceiver, not specified in detail, for example a radio antenna, of the smartphone 32.

The smartphone 34 has an integrated controller which is essentially formed by a microcontroller with an application software 38 implemented for the software-based evaluation of signals and data transmitted by means of the communication link 32. The application software 38 is preferably a mobile app or a smartphone app, which is stored in a data store of the controller. During operation, the controller displays the application software 38 on the display unit 36, which is designed as a touch screen, wherein the application software 38 can be operated by a hearing aid system user 2 using the touch-sensitive surface of the display unit 36.

Using the flowchart shown in FIG. 3, a method 40 according to the invention for operating the hearing aid 2 is explained in more detail in the following.

The method 40 is suitable and configured in particular to protect or warn a hearing aid system user 2 against an impending fall. In normal operation of the hearing aid device 2 the individual devices 6a and 6b of the hearing aid 4 are worn on the ears of the hearing aid system user. In this case, the individual devices 6a and 6b are coupled for bi-directional signal transmission via the communication links 8. The individual devices 6a and 6b are in this case also optionally connected for signal transmission to the smartphone 34 via the communication link 32.

According to the method, a movement of the hearing aid system user 2 or a movement event is first analyzed and/or characterized. Based on the evaluation or analysis, a probability of a future fall event, i.e. a fall risk, is determined for the hearing aid system user. This fall risk is compared with a stored threshold value and a perceptible warning signal is generated if the threshold value is reached or exceeded. For example, the warning signal is a warning tone generated by the hearing aid 4 and/or the smartphone 34. In addition or alternatively, the warning signal is implemented as a push notification and/or a haptic vibration signal of the smartphone 34.

The method is preferably at least partially executed by a controller, the method being executed in the hearing aid 4 and/or in the smartphone 34, for example. In other words, the controller is part of the signal processing 16 or the smartphone 34, for example. It is also conceivable, for example, that the method is carried out partly in the hearing aid 4 and partly in the smartphone 34, i.e. that both the hearing aid 4 and the smartphone 34 have such a controller. For this purpose, data is sent from the hearing aid 4 to the smartphone 34 and back via the communication link 32.

The analysis and evaluation of the movement can be carried out in a plurality of steps, for example, enabling a particularly safe and reliable determination of the fall risk. FIG. 3 shows a sequence of a series of method steps, wherein, for example, the steps can be executed at least partially in a different order and/or at least partially in parallel.

For example, in a method step 42, the motion data 26 is first acquired and evaluated. This means that the movement of the hearing aid system user 2 is analyzed in a current situation using the motion sensor 24. For example, the analysis or evaluation is carried out separately for both individual devices 6a, 6b or else the movement data 26 of both individual devices 6a, 6b is analyzed in combination.

In a method step 44, the current acoustic environmental situation is analyzed based on the audio signals 14. This analysis or evaluation is preferably carried out in parallel with the evaluation of the movement data 26. The current environmental situation is assigned to the current movement data 26 in a suitable manner and stored in a memory, not shown in detail.

In a method step 46, the current movement data 26 and environmental situation are compared, for example, with previous or stored movement data 26 in comparable and different environmental situations in order to detect deviations or abnormalities in the movement patterns, for example. Such deviations or abnormalities are an indication of an increased fall risk.

For example, in an optional method step 48, user feedback is requested based on the result of the method step 44. This is carried out, for example, by means of the application software and/or by voice commands. For example, this feedback is requested when an unknown movement pattern and/or an unknown acoustic environmental situation is detected.

Preferably, personal health data of the hearing aid system user is stored in a memory of the hearing aid system 2. In a method step 50, this health data is taken into account in the movement pattern analysis. For example, a movement pattern analysis of the movement data 26 is performed in relation to dementia or vertigo.

In the optional method step 52, an input is captured—if available—from other sensors connected to the hearing aid system 2, such as photoplethysmography (PPG), electroencephalography (EEG), electromyography (EMG), which provide information about the cardiovascular status (i.e. frequency, heart rate variability) of the hearing aid system user 2 and/or stress measurements.

In another optional method step 54, the current movement data 26 is compared with other similar user data, which is stored anonymously, i.e. not attributable to a user, in a cloud. The method step 54 corresponds, for example, to the method step 46, wherein this is not stored data of the hearing aid system user 2 him/herself, but data of other users that can be accessed in the cloud. This allows comparable data from other users to be also taken into account for determining the fall risk, which provides a more robust and reliable prediction of the fall probability.

In a method step 56, a user profile is created for the hearing aid system user based on the stored movement data and environmental situations. In other words, the hearing aid system user is "classified" to a profile based on the stored data. This enables a daily routine detection to compare a current result with previous results, and thus to track and detect changes. The user profile enables an improved and more robust determination of the fall risk.

In a method step 58, the hearing aid settings, i.e. hearing aid parameters and/or hearing aid performance, are adjusted according to the method steps 46 and/or 54. The adapted hearing aid output can be used as a contribution to a fall intervention or fall prevention (e.g. in the case of dementia or other disorders). Changing the hearing aid settings can contribute to an improved orientation and/or reducing the number of distractors, thereby reducing the fall risk. For example, in method step 58, the currently determined fall risk is compared with a (second) threshold value, which is chosen smaller than the (first) threshold value for triggering the warning signal. If this (second) threshold value is reached or exceeded, the hearing aid settings are changed and adjusted. This means that before the warning signal is issued, a further preventative measure is carried out to reduce the fall risk. Preferably, a correlative or gradual adjustment of the hearing aid settings is implemented with increasing fall probability.

In a possible embodiment of the method, measures to reduce the fall risk are indicated on the auxiliary device when the (first or second) threshold value is reached or exceeded. In a method step 60, the hearing aid system user 2 is offered treatments or tips provided by the application software 38 of the smartphone 34, dependent on the movement data 26 and/or the fall risk. For example, based on the gait analysis, the display unit 36 displays actions that contribute to maintaining or increasing physical fitness to reduce the fall risk, or that slow cognitive decline, or encourage healthy aging or a good quality of life, or support other interventions such as taking doses of pharmaceutical interventions.

In a method step 62, on the basis of the evaluated movement data 26, changes in the movement patterns and/or the fall risk as well as a current status are shown on the display unit 36 of the smartphone 34. In this way, the hearing aid system user 2 can monitor their own fall risk. This is particularly advantageous if the method is used to monitor another ANS disorder of the hearing aid system user 2, so that the hearing aid system user 2 can monitor their health status or course of illness even without a doctor's visit.

In a method step 64, a "classification" for the hearing aid is adjusted according to the user profile, thereby providing improved output for the hearing aid system user 2. This means that, based on the user profile created in method step 56, the stored preferences of the hearing aid 4 for different environmental situations are adapted to minimize the fall risk in these situations. In contrast to the method step 58, in which the current hearing aid settings are adjusted, in method step 64 the hearing aid settings assigned to the different acoustic environmental situations are modified. This means that already improved hearing aid settings relating to the fall risk will be used in a future change of environment.

In an optional method step 66, the movement analysis and the fall risk are transmitted to a service provider of the healthcare system, for example, a doctor or medical professional. This allows remote monitoring of ANS disorders of the hearing aid system user, for example. Preferably, this method step 66 is only carried out if the hearing aid system user has given the appropriate consent or approval.

Based on FIGS. 4 to 6, movement data 26 for different movement events are shown in the following. The movement data 26 in this case is recorded with a binaural hearing aid 4 which is equipped with a motion sensor 24, in particular a 3D acceleration sensor. The figures show the movement data 26 for "stationary exercises". The movement data 26 of FIG. 4 shows a case of standing up from a chair, i.e. a movement transition from sitting to standing. FIG. 5 shows the signal or data curve for a turning test, and FIG. 6 shows movement data 26 of a standing-still test.

FIG. 4 comprises two sections 68, 70, arranged vertically on top of each other, each showing a time-acceleration diagram. In sections 68, 70, the time t is plotted horizontally, i.e. along the abscissa axis (X-axis), for example in seconds, and an acceleration B is plotted along the vertical ordinate axis (Y-axis). Positive acceleration values correspond to acceleration and negative acceleration values to deceleration. Sections 68, 70 show raw measurement data of a 3-axis accelerometer (3D acceleration sensor), normalized to the acceleration due to gravity G (1 G=9.81 m/s²).

In sections 68, 70, the movement data 26 is represented by three curves 72, 74, 76, wherein the curve 72 shows the acceleration B along an X direction and the curve 74 shows the acceleration B along a Y direction, and the curve 76 shows the acceleration B along a Z direction.

For example, the X, Y, and Z directions refer to the three main families of body planes, i.e. the transverse planes (XY), frontal planes (YZ), and sagittal planes (XZ). For example, the abscissa axis (X axis, X direction) is oriented along the sagittal direction (front to back) and the ordinate axis (Y axis, Y direction) along the transverse direction (left to right), and the applicator axis (Z axis, Z direction) along the longitudinal direction (top to bottom).

Sections 68, 70 show the movement data 26 for two situations, wherein only the monaural movement data for one of the individual devices 6a, 6b, for example the individual device worn on the left ear, is shown.

The curves 72, 74, 76 in section 68 show the movement data 26 in the case where the hearing aid system user stands up from a chair in a normal manner and then sits down again, twice.

Section 70 shows the same curves for standing and then sitting down twice, wherein the hearing aid system user in this case has supported him/herself on an armrest to simulate a unilateral disability.

In the normal case of section 68, accelerations along the Z and X directions are shown. The X component is due to acceleration caused by the forward inclination of the body, while the Z component describes the accelerations due to the lifting or moving of the body. In the armrest-supported case of section 70, the X component is similar to the first case. However, the Z component is much less pronounced. In addition, there is also a Y component, which shows that there was a significant movement to the side. Overall, the time interval for the sequence for the supported case also lasts longer (1-2 seconds) compared to the normal case (<1 second).

By evaluating and analyzing the movement data 26 or the curves 72, 74, 76, it is thus possible to quantify and distinguish different types of standing up/sitting down with hearing aid systems 2 which are equipped with an accelerometer 24.

FIG. 5 comprises two sections 78, 80, arranged vertically on top of each other, each showing a time-acceleration diagram. In sections 68, 70, the time t is plotted horizontally, i.e. along the abscissa axis (X-axis), for example in seconds, and an acceleration difference ΔB is plotted along the vertical ordinate axis (Y-axis). The acceleration difference ΔB is the difference between the accelerations of the left and right individual devices 6a, 6b, i.e. the binaural difference, which means the acceleration of the left device minus the acceleration of the right device, the acceleration difference ΔB being normalized to the acceleration due to gravity G.

In sections 78, 80, the movement data 26 are represented by three curves 82, 84, 86, wherein the curve 82 shows the acceleration difference ΔB along the X direction, the curve 84 shows the acceleration difference ΔB along the Y direction, and the curve 86 shows the acceleration difference ΔB along the Z direction.

The turning behavior of a person is associated with the fall risk. Sections 78, 80 show the ability to measure approximately 90° body rotations with accelerometer data for a binaural configuration. Sections 78, 80 show the movement data for the turn sequence 90° left, 90° right, 90° left, 90° right.

The curves 82, 84, 86 of section 78 show the movement data for turns at normal speed and the curves 82, 84, 86 of section 80 show the movement data for turns at slow speed.

In the normal speed case of section 78, significant acceleration peaks are visible in the X and Y components, which represent the tangential and radial forces of the rotation of the body. In the slow speed case of section 80, the peaks are less pronounced or are essentially imperceptible.

FIG. 5 shows that body rotations at normal speed can be distinguished from body rotations at slow speed when only a binaural configuration and accelerometers are used. In the case of body rotations at normal speed, the maneuver is detected reliably and in a qualified manner (speed, duration, rotation angle).

FIG. 6 contains three horizontal sections 88, 90, 92 arranged next to one another, each showing a two-dimensional acceleration diagram. In sections 88, 90, 92, an acceleration Bx in the X direction is plotted horizontally, i.e. along the abscissa axis (X-axis), and an acceleration By in the Y direction is plotted along the vertical ordinate axis (Y-axis) in units of the acceleration due to gravity G.

Sections 88, 90, 92 show a standstill test in which a hearing aid system user maintains his/her body in balance while standing normally. Sections 88, 90, 92 show a temporal curve 94 of accelerations for a measurement duration of about one minute (1 min) for a healthy test subject. Section 88 shows a normal standing pose, while section 90 shows a standing pose in which the test subject has closed their eyes. The movement data of section 92 show a one-legged standing pose, i.e. standing on one leg, with the eyes open.

Sections 88, 90, 92 show the zero-mean accelerometer data in the XY plane for a monaural acceleration measurement. Perfect balancing skills would result in a point at the origin (0, 0). Large fluctuations in the curves are signs of a greater need to regulate the balance.

The movement data in section 88 show a cluster centered at the origin, with a flat overall shape. The movement data has greater variations in the X component than in the Y component, which corresponds to a dominant left/right fluctuation and less pronounced forward/backward fluctuations.

The movement data in section 88 show two clusters distributed around the origin. Due to the closed eyes, a visual reference point is missing and the balance is only maintained by the equilibrium system. This causes the test person to get into semi-stable states until the fluctuations become too large and stabilize in another semi-stable state.

The movement data in section 90 show a cluster close to the origin. The overall shape of the cluster is more circular compared to the standing pose (section 88), with left/right and front/back fluctuations evident, which indicate a more dynamic muscular regulation to maintain the balance.

For example, it is conceivable in the context of the method 40 to perform at least the normal standing scenario every day, with deviations from typical results, for example, indicating a bad day with an increased fall risk.

The invention is not limited to the exemplary embodiments described above. Instead, other variants of the invention can also be derived from them by the person skilled in the art, without departing from the subject-matter of the invention. In particular, all individual features described in connection with the exemplary embodiments can also be combined together in different ways without departing from the subject matter of the invention.

LIST OF REFERENCE SIGNS

2 hearing aid system
4 hearing aid
6a, 6b individual device
8 communication link
10 device housing
12 input transducer
14 acoustic data/audio signal
16 signal processing signal
18 output signal
20 output transducer
22 battery
24 motion sensor
26 movement data
28, 30 transceiver
32 communication link
34 auxiliary device/smartphone
36 display unit
38 application software
40 method
42 . . . 66 method step
68, 70 section
72, 74, 76 curve
78, 80 section
82, 84, 86 curve
88, 90, 92 section
94 curve
t time
B, Bx, By acceleration
ΔB acceleration difference

The invention claimed is:

1. A method of operating a hearing aid system having a hearing aid with at least one input transducer, an output transducer, and a motion sensor, the method comprising:
    capturing a movement of a hearing aid system user as movement data of the motion sensor;
    determining a probability of a future fall or trip event on the part of the hearing aid system user on a basis of the movement data;
    generating a perceptible warning signal when the probability reaches or exceeds a stored threshold value; and
    adjusting a hearing aid parameter and/or a hearing aid performance of the hearing aid depending on the probability of the future fall or trip event by varying settings of the hearing aid with regard to signal processing and output of an ambient signal in the event of a change in a risk of falling so as to minimize the risk of falling.

2. The method according to claim 1, which comprises storing personal health data of the hearing aid system user in a memory of the hearing aid system and determining the probability on a basis of the personal health data.

3. The method according to claim 1, which comprises determining an environmental situation of the hearing aid system user on a basis of acoustic data of the input transducer, and assigning the movement data to the environmental situation and storing in a memory.

4. The method according to claim 3, wherein the step of determining the probability comprises comparing the movement data for a particular environmental situation with the stored movement data and environmental situations.

5. The method according to claim 3, which comprises creating a user profile for the hearing aid system user based on the stored movement data and environmental situations.

6. The method according to claim 1, wherein the hearing aid is a binaural hearing aid with two individual devices each having a respective motion sensor, and the method comprises: separately evaluating the movement data of the individual devices and subsequently combining to determine the probability.

7. The method according to claim 1, which comprises transmitting the movement data and/or the probability to an auxiliary device connected to the hearing aid for signal transmission.

8. The method according to claim 7, wherein the auxiliary device is a mobile display and control device and the method comprises: when the threshold value is reached or exceeded, displaying on the auxiliary device measures to reduce a risk of a fall or trip.

9. The method according to claim 1, which comprises acquiring the movement data for determining the probability during a specified movement pattern of the hearing aid system user.

10. A hearing system, comprising:
    a hearing aid with at least one input transducer for receiving an acoustic ambient signal, and with an output transducer for outputting an acoustic signal, and with a motion sensor for detecting a movement of a hearing aid system user; and a controller configured for carrying out the method according to claim 2.

11. The hearing system according to claim 10, wherein the hearing system is a hearing aid.

12. A method of operating a hearing aid system having a hearing aid with at least one input transducer, an output transducer, and a motion sensor, the method comprising:

capturing a movement of a hearing aid system user as movement data of the motion sensor;

determining a probability of a future fall or trip event on the part of the hearing aid system user on a basis of the movement data;

generating a perceptible warning signal when the probability reaches or exceeds a stored threshold value; and adjusting a hearing aid parameter and/or a hearing aid performance of the hearing aid depending on the probability of the future fall or trip event;

determining an environmental situation of the hearing aid system user on a basis of acoustic data of the input transducer, and assigning the movement data to the environmental situation and storing in a memory; and wherein the step of determining the probability comprises comparing the movement data for a particular environmental situation with the stored movement data and environmental situations.

13. A method of operating a hearing aid system having a hearing aid with at least one input transducer, an output transducer, and a motion sensor, the method comprising:

capturing a movement of a hearing aid system user as movement data of the motion sensor;

determining a probability of a future fall or trip event on the part of the hearing aid system user on a basis of the movement data;

generating a perceptible warning signal when the probability reaches or exceeds a stored threshold value; and adjusting a hearing aid parameter and/or a hearing aid performance of the hearing aid depending on the probability of the future fall or trip event;

determining an environmental situation of the hearing aid system user on a basis of acoustic data of the input transducer, and assigning the movement data to the environmental situation and storing in a memory; and creating a user profile for the hearing aid system user based on the stored movement data and environmental situations.

\* \* \* \* \*